(12) United States Patent
Yokomori et al.

(10) Patent No.: US 6,365,783 B1
(45) Date of Patent: Apr. 2, 2002

(54) PROCESS FOR PRODUCING ALCOHOLS

(75) Inventors: Yorozu Yokomori, Tokyo; Tsukasa Hayashi; Toshiaki Ogata, both of Ichihara; Junichi Yamada, Chiba; Seiji Saito, Ichihara, all of (JP)

(73) Assignee: Kyowa Yuka Co., Ltd., Tokyo (JP)

( * ) Notice: Subject to any disclaimer, the term of this patent is extended or adjusted under 35 U.S.C. 154(b) by 0 days.

(21) Appl. No.: 09/577,981

(22) Filed: May 25, 2000

(30) Foreign Application Priority Data

May 31, 1999 (JP) .......................................... 11-150841

(51) Int. Cl.$^7$ ............................................... C07C 45/50
(52) U.S. Cl. ...................... 568/451; 568/491; 568/909
(58) Field of Search ................................ 568/451, 491, 568/909

(56) References Cited

U.S. PATENT DOCUMENTS

| | | | |
|---|---|---|---|
| 4,242,283 A | 12/1980 | Hibbel et al. | ................ 568/451 |
| 4,447,661 A | 5/1984 | Hoshiyama et al. | ......... 568/882 |

FOREIGN PATENT DOCUMENTS

| | | | |
|---|---|---|---|
| DE | 206370 | 5/1982 | .................... 29/16 |
| EP | 702204 | 1/1954 | |
| JP | 62-1930 | 1/1987 | |

OTHER PUBLICATIONS

Tamas et al, Journal of Mol.Catal., 85(2), pp. 121–9 (1993).*

* cited by examiner

*Primary Examiner*—Sreeni Padmanabhan
(74) *Attorney, Agent, or Firm*—Fitzpatrick, Cella, Harper & Scinto

(57) ABSTRACT

Provided is a process for producing alcohols or aldehydes by reacting monoolefins with carbon monoxide and hydrogen with less formation of by-products. The process comprises the step of reacting a monoolefin with carbon monoxide and hydrogen in the presence of a cobalt carbonyl catalyst until the conversion of monoolefin reaches 50–90% (the first reaction step), the step of separating unreacted monoolefin from the reaction mixture obtained in the first reaction step (the step of separation of unreacted monoolefin) and the step of reacting the separated unreacted monoolefin with carbon monoxide and hydrogen in the presence of a cobalt carbonyl catalyst (the second reaction step), wherein at least one of the first reaction step and the second reaction step is carried out in the presence of water.

12 Claims, 1 Drawing Sheet

PROCESS FOR PRODUCING ALCOHOLS

BACKGROUND OF THE INVENTION

The present invention relates to a process for producing alcohols or aldehydes by reacting monoolefins with carbon monoxide and hydrogen.

So far, the method, for producing saturated aliphatic aldehydes and saturated aliphatic alcohols both having one more carbon atom than monoolefins by reacting the monoolefins with carbon monoxide and hydrogen (oxo synthesis reaction), which is known as the oxo synthesis process, has been widely employed. The alcohols obtained by this reaction are useful as raw materials for plasticizers, intermediate materials for agricultural chemicals, medicines and food additives, etc.

It is known that a cobalt carbonyl catalyst is useful in the above method for producing alcohols. The method using a cobalt carbonyl catalyst has advantages in that the rate of reaction is high and the recovery of the catalyst is easy, but also has the defect that large quantities of by-products are formed because of the use of the cobalt carbonyl catalyst having a high acidity. In the early stage of the reaction, a saturated aliphatic aldehyde having one more carbon atom than a monoolefin as a starting material is formed as the main product from the monoolefin, and then a saturated aliphatic alcohol having one more carbon atom than said monoolefin is formed by hydrogenation. Further, said aldehyde reacts with said alcohol to form an acetal, which causes formation of acetal-derived by-products. The acetal is readily hydrolyzed to form an aldehyde and an alcohol in an acidic aqueous solution. However, an ether, an ether aldehyde and an ether alcohol are also formed from the acetal as by-products which can not be utilized to produce the alcohol or aldehyde. Therefore, the problem with this method is to inhibit the formation of acetal and acetal-derived by-products. Shown below is a flow chart of the formation of by-products in the above-described oxo synthesis reaction.

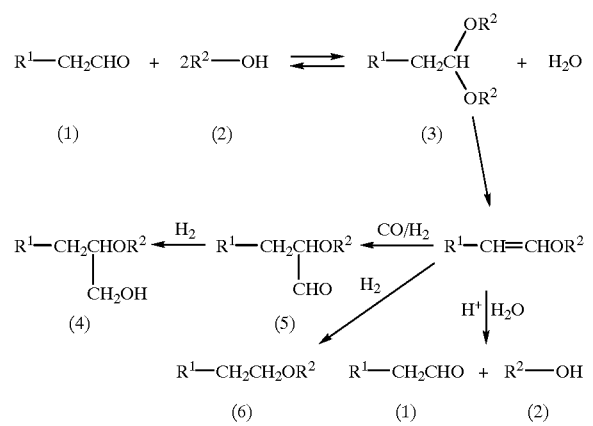

(1) saturated aliphatic aldehyde having one more carbon atom than olefin as a starting material
(2) saturated aliphatic alcohol having one more carbon atom than olefin as a starting material
(3) acetal
(4) ether alcohol
(5) ether aldehyde
(6) ether
(In the formula, $R^1$ and $R^2$ represent alkyl, etc., wherein $R^2$ is alkyl, etc. having two more carbon atoms than $R^1$.)

As a solution to the above problem, Japanese Published Examined Patent Application No. 1930/87 discloses a process in which water is added to the reaction system to inhibit a side reaction from acetal in-the presence of a hydrocobalt tetracarbonyl catalyst. However, this process is not satisfactory for practical use because an aldehyde and an alcohol coexist in the reaction system for such a long time that an acetal and acetal-derived by-products are formed in large quantities.

Japanese Published Examined Patent Application No. 57414/83 describes a process in which monoolefin remaining unreacted after the oxo synthesis reaction is further subjected to reaction in a high pressure gas separator. However, this process is not satisfactory for practical use either, because a special apparatus, i.e. a high pressure gas separator is necessary, and also in respect of the selectivity of monoolefin for aldehyde or alcohol and the formation of by-products.

Further, U.K. Patent No. 702,204B discloses a process for producing an oxygen-containing compound in which an olefin is subjected to reaction with carbon monoxide and hydrogen in the presence of a cobalt catalyst, and unreacted monoolefin is separated from the obtained reaction mixture and then subjected to reaction with carbon monoxide and hydrogen in the presence of a cobalt catalyst. However, this process is not satisfactory for practical use either, in respect of the selectivity of monoolefin for aldehyde or alcohol and the formation of by-products.

An object of the present invention is to provide a process for producing alcohols or aldehydes by reacting monoolefins with carbon monoxide and hydrogen which is suitable for industrial production in respect of formation of by-products and selectivity of a starting material for the desired product.

SUMMARY OF THE INVENTION

The present invention relates to a process for producing an alcohol or an aldehyde in which a monoolefin is used as a starting material to produce a saturated aliphatic alcohol or saturated aliphatic aldehyde having one more carbon atom than the monoolefin, comprising the step of reacting the monoolefin with carbon monoxide and hydrogen in the presence of a cobalt carbonyl catalyst until the conversion of monoolefin reaches 50–90% (the first reaction step), the step of separating unreacted monoolefin from the reaction mixture obtained in the first reaction step (the step of separation of unreacted monoolefin) and the step of reacting the separated unreacted monoolefin with carbon monoxide and hydrogen in the presence of a cobalt carbonyl catalyst (the second reaction step), wherein at least one of the first reaction step and the second reaction step is carried out in the presence of water.

Figure 1:
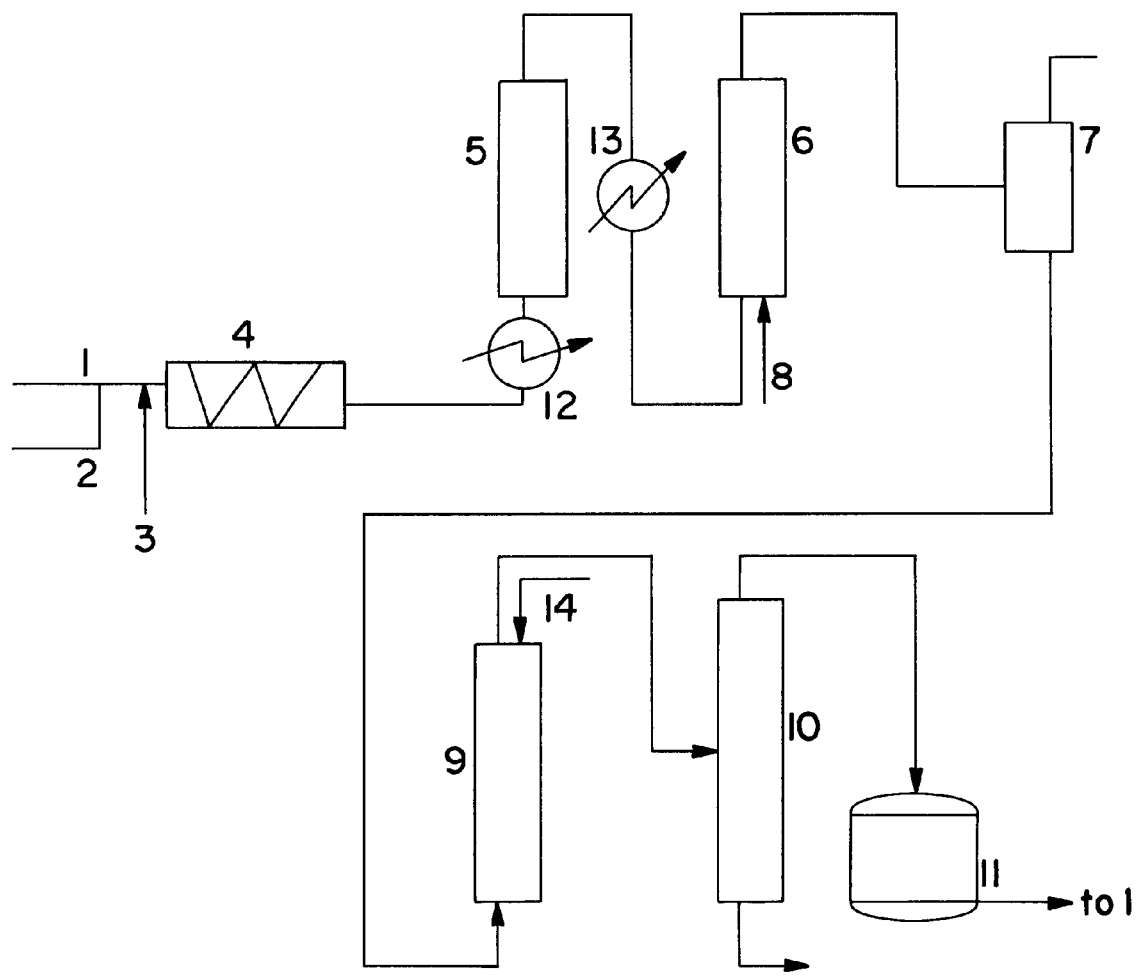
FIG. 1 is a flow chart of an industrial continuous reactor for the process of the present invention.

The numbers in FIG. 1 represent the following: 1, pipe for feeding monoolefin; 2, pipe for feeding gas mixture of hydrogen and carbon monoxide; 3, pipe for feeding water; 4, static mixer; 5, reaction column; 6, cobalt-removing column; 7, vapor-liquid separator; 8, pipe for feeding aqueous solution of sodium hydroxide; 9, washing column; 10, 20-plate continuous distillation column; 11, receiver; 12, heat exchanger; 13, heat exchanger; 14, pipe for feeding aqueous solution of sodium hydroxide.

DETAILED DESCRIPTION OF THE INVENTION

The monoolefins to be used as a starting material in the process of the present invention are hydrocarbons having one double bond between carbon atoms. Preferably the monoolefins are straight-chain, branched or alicyclic monoolefins having 3–20 carbon atoms, more preferably straight-chain or branched monoolefins having 3–20 carbon atoms, and most preferably straight-chain or branched monoolefins having 3–10 carbon atoms. Examples of the preferred monoolefins include propylene, butene, isobutene, pentene, hexene, heptene, octene, nonene and decene. There may be various stereoisomers or optical isomers for the monoolefins, and mixtures of such isomers may also be used as a starting material. For example, mixtures of propylene dimers such as hexene, 2-methylpentene, 3-methylpentene, 4-methylpentene and 2,3-dimethylbutene, and mixtures of butene dimers such as octene, 2-methylheptene, 3-methylheptene, 2,4-dimethylhexene, 3,4-dimethylhexene and 2,3,4-trimethylpentene may be used.

In the first reaction step, the monoolefin is subjected to reaction with hydrogen and carbon monoxide in the presence of a cobalt carbonyl catalyst. The reaction temperature is preferably 120–200° C., more preferably 140–170° C., and the reaction pressure is preferably 50–350 kg/cm$^2$, more preferably 150–330 kg/cm$^2$. The ratio of hydrogen gas to carbon monoxide gas ($H_2$/CO: molar ratio) is preferably 0.8–2, more preferably 1–1.6.

The cobalt carbonyl catalysts that may be used in the process of this invention are those used in ordinary oxo synthesis, and examples thereof include hydrocobalt tetracarbonyl and dicobalt octacarbonyl. The catalysts are used in such an amount that the cobalt metal content is preferably 0.1–1.0 wt %, more preferably 0.2–0.6 wt % based on monoolefin.

The reaction in the first reaction step is stopped when the conversion of monoolefin reaches 50–90%. The conversion of monoolefin is calculated from analytical values obtained by gas chromatography or the like according to the following equation.

Conversion of monoolefin (%)=$(X-Y)/X \times 100$(%)

X: monoolefin as a starting material (mole)
Y: unreacted monoolefin (mole)

After the reaction is stopped, it is preferred to remove the cobalt carbonyl catalyst from the reaction mixture by extraction or decomposition in the following manner. To the reaction mixture is added an aqueous solution of an alkali metal compound or an aqueous solution of an alkaline earth metal compound for extraction to remove the cobalt carbonyl catalyst. The concentration of the alkali metal compound or alkaline earth metal compound in the aqueous solution is 0.1–4 wt %, preferably 1–2 wt %. The aqueous solution is added to give the alkali metal/cobalt atomic ratio (molar ratio) of 1–5, preferably 1–2, or the alkaline earth metal/cobalt atomic ratio (molar ratio) of 0.5–2.5, preferably 0.5–1. Examples of the alkali metal compounds and the alkaline earth metal compounds include hydroxides and metallic salts of lithium, sodium, potassium, magnesium and calcium. By removing the cobalt carbonyl catalyst by the above method, the conversion of the acetal formed during the reaction into an ether or an ether aldehyde can be substantially prevented.

In order to remove the cobalt carbonyl catalyst by the above method, it is necessary to keep the pressure at such a level that the cobalt carbonyl catalyst can exist stably, preferably 50 kg/cm$^2$ or more as the carbon monoxide partial pressure. The removal of the cobalt carbonyl catalyst is preferably carried out at a temperature of 100–140° C.

Then, the step of separating unreacted monoolefin from the reaction mixture obtained in the first reaction step as such or freed of the cobalt carbonyl catalyst (the step of separation of unreacted monoolefin) is carried out.

Usually, separation of unreacted monoolefin from the reaction mixture can be carried out by means of distillation, etc. The conditions for distillation are not specifically restricted, but are properly selected depending upon the material to be distilled. The unreacted monoolefin distillate separated in the above step may contain paraffin and can be used as such as a starting material for the second reaction step. The reaction mixture freed of the unreacted monoolefin mainly comprises the desired alcohol or aldehyde. This mixture is hydrogenated with a copper-chromium catalyst composed of copper oxide and chromium oxide or a nickel catalyst such as Raney nickel to obtain a mixture containing the desired alcohol as a main component.

The separated unreacted monoolefin is subjected to reaction with hydrogen and carbon monoxide in the presence of a cobalt carbonyl catalyst (the second reaction step). The conditions for the reaction such as the temperature, the pressure, the ratio of hydrogen gas to carbon monoxide gas and the amount of the cobalt carbonyl catalyst can be selected according to the conditions in the above first reaction step.

In the second reaction step, it is preferred to carry out the reaction until the conversion of the unreacted monoolefin reaches 90% or more.

After the second reaction step is stopped, it is preferred to remove the cobalt carbonyl catalyst from the obtained reaction mixture in the same manner as described above.

In at least one of the first reaction step and the second reaction step, the reaction is carried out in the presence of water. The amount of water to be used is preferably 0.5–30 wt %, more preferably 1–10 wt % based on monoolefin. When water is used, a solvent such as methanol, ethanol, propanol, tetrahydrofuran or dioxane may be used in an amount of 0.1–5 wt % based on water. Further, surfactants such as polyoxyethylene lauryl ether, polyoxyethylene octyl ether and polyoxyethylene nonylphenol ether may be used in an amount of 0.01–0.5 wt % based on monoolefin. It is preferred that water be present in the reaction system in the dissolved state or in particles having a diameter of 0.5 mm or less.

It is preferred to carry out the second reaction step, wherein the content of by-products in the reaction system is higher, in the presence of water.

When a column type continuous reactor is used as a reactor, it is preferred that a mixture of a gas mixture of hydrogen and carbon monoxide and monoolefin flows at a linear velocity of 0.5 m/sec. or more In the process of the present invention, a formic acid ester derived from the desired aldehyde is formed by the reaction, and this formic acid ester can be easily converted into the desired alcohol by known hydrogenation methods, for example, catalytic reduction using palladium-carbon, etc. as a catalyst and a method using reducing reagents such as lithium aluminum hydride.

According to the process of the present invention, an alcohol and an aldehyde coexist in the reaction system for only a short time, which reduces the formation of an acetal and acetal-derived by-products to trace amounts, and a saturated aliphatic alcohol or saturated aliphatic aldehyde having one more carbon atom than a monoolefin as a starting material can be obtained in high yields.

By the process of the present invention, usually an alcohol and an aldehyde are produced as the desired main products, but an alcohol or an aldehyde alone may be produced as the single desired product.

The reaction mixture which mainly comprises an alcohol and an aldehyde obtained by the process of the present invention is subjected to hydrogenation reaction, as may be required, to obtain a reaction mixture mainly comprising the alcohol. The obtained mixture is purified by means of distillation, etc. to separate the alcohol. The alcohol can be used as a raw material for plasticizers, an intermediate material for agricultural chemicals, medicines and food additives, etc.

Alternatively, the reaction mixture mainly comprising an alcohol and an aldehyde obtained by the process of the present invention is subjected to distillation, etc. to separate the alcohol and the aldehyde. The alcohol can be used for the same purpose as mentioned above and the aldehyde can be used as a starting material for organic acids, diols, etc.

Certain embodiments of the present invention are illustrated in the following examples. These examples are not to be construed as limiting the scope of the invention.

EXAMPLE 1

A. First Reaction Step

As a starting material, 240 g of propylene dimers (composition: 92% 2-methylpentene-1, 2% n-hexene mixture, 2% 2,3-dimethylbutene mixture, 1% 4-methylpentene mixture and 3% other propylene dimers; herein the term mixture means a mixture of monoolefins having a double bond at different positions, for example, n-hexene mixture means a mixture of n-hexene-1, n-hexene-2 and n-hexene-3, 2,3-dimethylbutene mixture means a mixture of 2,3-dimethylbutene-1 and 2,3-dimethylbutene-2, and 4-methylpentene mixture means a mixture of 4-methylpentene-1, 4-methylpentene-2 and 4-methylpentene-3; % means wt%; hereinafter, as for the composition of monoolefins as a starting material, the term mixture has the same significance as above and % means wt %) was put into a 500 ml stainless stirring autoclave.

Further, 0.24 g of dicobalt octacarbonyl (Kanto Chemical Co., Ltd.) was put into the autoclave, followed by replacement of an atmosphere with nitrogen. Then, a mixture of hydrogen gas and carbon monoxide gas ($H_2$/CO=1.3: molar ratio; hereinafter the gas mixture ratio is expressed in molar ratio) was fed so that the pressure inside the autoclave becomes 120 kg/cm$^2$. The autoclave was put into an electric furnace and the temperature was gradually raised. When the temperature of the reaction mixture reached about 120° C., gas absorption started gradually, after which time the feeding of the gas mixture was controlled to keep the pressure inside the autoclave constant at 160 kg/cm$^2$. After 30 minutes, the temperature of the reaction mixture reached 140° C., at which time the autoclave was cooled. When the temperature of the reaction mixture became 120° C., 6.91 ml of a 1.2 wt % aqueous solution of sodium hydroxide was pressed into the autoclave, followed by stirring for 30 minutes. The autoclave was cooled to room temperature and then depressurized, and the contents were taken out. After washing with water, the contents were analyzed by gas chromatography under the following conditions, whereby it was found that the conversion of monoolefins was 75.6%. In the gas chromatography, normal undecane was used as an internal standard.

Conditions for gas chromatography

Column: Capillary Column CP-SIL (GL Sciences) diameter 0.25 mm×length 25 m

Temperature: 80–280° C. (increase in temperature: 5° C./minute)

Analysis by gas chromatography was carried out under the above conditions also in the following examples and comparative examples.

B. Step of Separation of Unreacted Monoolefin

The contents in the autoclave obtained in the first reaction step were subjected to batch distillation by the use of a 20-plate distillation column at an atmospheric pressure at an overhead temperature of 60–150° C., whereby 24 g of an unreacted propylene dimers-paraffins mixture was recovered. The amount of the unreacted monoolefins was calculated from the bromine number.

C. Second Reaction Step

The mixture of the recovered unreacted propylene dimers and paraffins (24 g: 89.2% unreacted monoolefins, 10.8% paraffins) was put into a 100 ml stainless stirring autoclave, and 0.08 g of dicobalt octacarbonyl (Kanto Chemical Co., Ltd.) was added thereto. To the resulting mixture was further added 5 g of deoxidized water, followed by replacement of an atmosphere inside the autoclave with nitrogen. Then, a mixture of hydrogen gas and carbon monoxide gas ($H_2$/CO=1.3) was fed so that the pressure inside the autoclave becomes 120 kg/cm$^2$. The autoclave was put into an electric furnace and the temperature was gradually raised. When the temperature reached around 120° C., gas absorption started gradually. The above gas mixture was fed so that the pressure inside the autoclave can be kept constant at 160 kg/cm$^2$. One hour after the attainment of a temperature of 150° C., the conversion of monoolefins reached 98%. Then, the autoclave was cooled to 120° C., and 2.3 ml of a 1.2 wt % aqueous solution of sodium hydroxide was pressed therein, followed by stirring for 30 minutes. The autoclave was cooled to room temperature and then depressurized, and the contents were taken out. After washing with water, the contents were analyzed by gas chromatography.

Comparative Example 1

After 24 g of propylene dimers having the same composition as those of Example 1 was put into a 100 ml stainless stirring autoclave, 0.1 g of dicobalt octacarbonyl (Kanto Chemical Co., Ltd.) was added thereto, followed by replacement of an atmosphere inside the autoclave with nitrogen. A mixture of hydrogen gas and carbon monoxide gas ($H_2$/CO=1.3) was fed so that the pressure inside the autoclave becomes 120 kg/cm$^2$. The autoclave was put into an electric furnace and the temperature was gradually raised. When the temperature reached around 120° C., gas absorption started gradually. The above gas mixture was continuously fed through a control valve so that the pressure inside the autoclave can be kept constant at 160 kg/cm$^2$. One hour after the attainment of a temperature of 150° C., the conversion of monoolefins reached 98.6%. Then, the autoclave was cooled to 120° C., and 2.9 ml of a 1.2 wt % aqueous solution of sodium hydroxide was pressed therein with a pump, followed by stirring for 30 minutes. The autoclave was cooled to room temperature and then depressurized, and the contents were taken out. After washing with water, the contents were analyzed by gas chromatography.

Comparative Example 2
(Method described in Japanese Published Examined Patent Application No. 1930/87)

The same procedure as in Comparative Example 1 was repeated, except that 6 g of water was added to the starting material.

Comparative Example 3
(Method described in U.K. Patent No. 702,204B)

The same procedure as in Example 1 was repeated, except that 5 g of water was not added in the second reaction step.

The compositions of the reaction products obtained in Example 1 and Comparative Examples 1–3 are shown in Table 1. The composition of each reaction product was analyzed by gas chromatography. "Total" in Table 1 indicates the composition of the total reaction product obtained in the first and second reaction steps. The alcohol, aldehyde, ether, ether aldehyde, ether alcohol, acetal and formic acid ester shown in Table 1 are those corresponding to monoolefins as a starting material. Formation of these products can be illustrated by the following reaction scheme when monoolefins having a double bond at the end are used. (The same shall apply to Tables 2–5.)

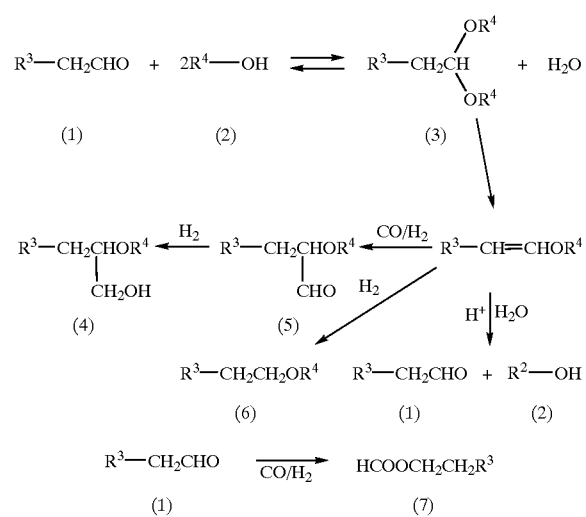

(1) saturated aliphatic aldehyde having one more carbon atom than olefin as a starting material
(2) saturated aliphatic alcohol having one more carbon atom than olefin as a starting material
(3) acetal
(4) ether alcohol
(5) ether aldehyde
(6) ether
(7) formic acid ester
(In the formula, $R^3$ represents alkyl, etc., and $R^4$ represents alkyl, etc. having two more carbon atoms than $R^3$.)

The selectivity of monoolefin was calculated according to the following equation.

Selectivity of monoolefin (%) = $Z/W \times 100$(%)

Z: Product (mole)
W: Monoolefin as a starting material (mole)

TABLE 1

| | (FIGS.: selectivity of monoolefin: %) | | | | | |
|---|---|---|---|---|---|---|
| | Example 1 | | | | | Comp. |
| | 1st reaction | 2nd reaction | Total | Comp. Example 1 | Comp. Example 2 | Example 3 Total |
| C6 paraffin | 1.67 | 4.45 | 2.76 | 3.05 | 2.96 | 3.06 |
| Olefin | 24.40 | 2.05 | 0.50 | 1.14 | 1.98 | 0.33 |
| Aldehyde | 62.14 | 47.14 | 73.64 | 63.77 | 63.67 | 70.91 |
| Alcohol | 4.88 | 29.09 | 11.98 | 17.62 | 18.98 | 10.89 |
| Formic acid ester | 2.45 | 8.35 | 4.49 | 5.35 | 5.47 | 5.01 |
| Ether + Ether aldehyde + Ether alcohol | 0.57 | 4.03 | 1.55 | 1.82 | 1.49 | 1.58 |
| Acetal | 3.89 | 4.89 | 5.08 | 7.25 | 5.45 | 8.22 |
| High-boiling prod. 1) | 4.46 | 8.92 | 6.64 | 9.07 | 6.94 | 9.80 |
| Yield 2) | | 85.62 | 81.39 | 82.65 | | 81.80 |

1) High-boiling product: ether + ether aldehyde + ether alcohol + acetal
2) Yield = [aldehyde (mole) + alcohol (mole)]/monoolefin (mole) × 100 (%)

The process of the present invention, as compared with those of comparative examples, gives higher yields of alcohol and aldehyde based on monoolefin with less formation of by-products such as an acetal, ether, ether aldehyde and ether alcohol.

EXAMPLE 2

The same procedure as in Example 1 was repeated, except that 240 g of butene dimers (composition: 65% 3-methylheptene mixture, 20% 3,4-dimethylhexene mixture, 6% 2,4-dimethylhexene mixture, 5% n-octene mixture, 2% 2-methylheptene mixture, 1.5% 2,3,4-trimethylpentene mixture and 0.5% other butene dimers) was used as a starting material, 0.3 g of dicobalt octacarbonyl and 8.6 ml of a 1.2 wt % aqueous solution of sodium hydroxide were used in the first reaction step, 0.1 g of dicobalt octacarbonyl and 2.9 ml of a 1.2 wt % aqueous solution of sodium hydroxide were used in the second reaction step, and the reaction temperature and time in the first reaction step were changed to 150° C. and 2 hours. The conversion of monoolefins was 72% in the first reaction step and 95% in the second reaction step.

Comparative Example 4

The same procedure as in Comparative Example 1 was repeated, except that. 24 g of butene dimers having the same composition as those of Example 2 was used as a starting material, and the reaction was carried out at a temperature of 150° C. for 3 hours.

Comparative Example 5
(Method described in Japanese Published Examined Patent Application No. 1930/87)

The same procedure as in Comparative Example 4 was repeated, except that 6 g of water was added in the reaction.

Comparative Example 6
(Method described in U.K. Patent No. 702,204B)

The same procedure as in Example 2 was repeated, except that 5 g of water was not added in the second reaction step.

EXAMPLE 3

The same procedure as in Example 2 was repeated, except that 4 g of water and 4 mg of polyoxyethylene lauryl ether were used in the second reaction step. The conversion of monoolefins was 68.0% in the first reaction step and 96.4% in the second reaction step.

The compositions of the reaction products obtained in Examples 2 and 3 and Comparative Examples 4–6 are shown in Tables 2 and 3. The composition of each reaction product was analyzed by gas chromatography under the same conditions as described above.

TABLE 2

(FIGS.: selectivity of monoolefin: %)

|  | Example 2 | | | Comp. Example 4 | Comp. Example 5 | Comp. Example 6 Total |
|---|---|---|---|---|---|---|
|  | 1st reaction | 2nd reaction | Total | | | |
| C8 paraffin | 2.20 | 5.60 | 3.77 | 4.50 | 4.90 | 3.60 |
| Olefin | 28.05 | 5.20 | 1.46 | 5.10 | 6.11 | 1.10 |
| Aldehyde | 53.75 | 28.89 | 61.85 | 19.46 | 28.31 | 50.01 |
| Alcohol | 6.50 | 35.09 | 16.34 | 34.00 | 31.54 | 21.09 |
| Formic acid ester | 3.00 | 10.60 | 5.97 | 8.33 | 6.30 | 7.99 |
| Ether + Ether aldehyde + Ether alcohol | 1.30 | 6.40 | 3.10 | 8.26 | 7.50 | 4.01 |
| Acetal | 5.20 | 8.22 | 7.51 | 20.35 | 15.34 | 12.20 |
| High-boiling prod. 1) | 6.50 | 14.62 | 10.60 | 28.61 | 22.84 | 16.21 |
| Yield 2) | | | 78.20 | 53.46 | 59.85 | 71.10 |

1) High-boiling product: ether + ether aldehyde + ether alcohol + acetal
2) Yield = [aldehyde (mole) + alcohol (mole)]/monoolefin (mole) × 100 (%)

TABLE 3

(FIGS.: selectivity of monoolefin: %)

|  | Example 3 | | |
|---|---|---|---|
|  | 1st reaction | 2nd reaction | Total |
| C8 paraffin | 2.18 | 5.33 | 3.88 |
| Olefin | 31.95 | 3.60 | 1.15 |
| Aldehyde | 50.80 | 29.57 | 60.25 |
| Alcohol | 5.95 | 37.77 | 18.02 |
| Formic acid ester | 2.88 | 9.39 | 5.88 |
| Ether + Ether aldehyde + Ether alcohol | 1.18 | 6.36 | 3.21 |
| Acetal | 5.06 | 7.61 | 7.61 |
| High-boiling prod. 1) | 6.24 | 13.97 | 10.82 |
| Yield 2) | | | 78.27 |

1) High-boiling product: ether + ether aldehyde + ether alcohol + acetal
2) Yield = [aldehyde (mole) + alcohol (mole)]/monoolefin (mole) × 100 (%)

The process of the present invention, as compared with those of comparative examples, gives higher yields of alcohol and aldehyde based on monoolefin with less formation of by-products such as an acetal, ether, ether aldehyde and ether alcohol.

EXAMPLE 4

The same procedure as in Example 1 was repeated, except that 240 g of propylene trimers (composition: 0.9% 2,2,5-trimethylhexene mixture, 0.2% 2,2,4-trimethylhexene mixture, 1.9% 2,3,5-trimethylhexene mixture, 2.9% 2,2-dimethylheptene mixture, 13.4% 2,2,3-trimethylhexene mixture, 0.7% 2,4-dimethylheptene mixture, 3.7% 2,6-dimethylheptene mixture, 17.3% 2,5-dimethylheptene mixture, 9.3% 3,5-dimethylheptene mixture, 4.9% 2-methyl-3-ethylhexene mixture, 16.1% 2,3-dimethylheptene mixture, 18.1% 3,4-dimethylheptene mixture, 1.7% 4-methyloctene mixture, 1.3% 2-methyloctene mixture, 1.6% 3-methyloctene mixture and 6.0% other propylene trimers) was used as a starting material, 0.5 g of dicobalt octacarbonyl and 14.3 ml of a 1.2 wt % aqueous solution of sodium hydroxide were used in the first reaction step, 0.15 g of dicobalt octacarbonyl and 4.4 ml of a 1.2 wt% aqueous solution of sodium hydroxide were used in the second reaction step, and the reaction temperature and time in the first reaction step were changed to 150° C. and 4 hours. The conversion of monoolefins was 67% in the first reaction step and 92.3% in the second reaction step.

Comparative Example 7

The same procedure as in Comparative Example 1 was repeated, except that 24 g of propylene trimers having the same composition as those of Example 4 was used as a starting material, and the reaction was carried out at a temperature of 150° C. for 5 hours.

The compositions of the reaction products obtained in Example 4 and Comparative Example 7 are shown in Table 4. The composition of each reaction product was analyzed by gas chromatography under the same conditions as described above.

TABLE 4

(FIGS.: selectivity of monoolefin: %)

|  | Example 4 | | | Comp. Example 7 |
|---|---|---|---|---|
|  | 1st reaction | 2nd reaction | Total | |
| C9 paraffin | 2.88 | 6.02 | 4.85 | 4.30 |
| Olefin | 32.80 | 7.71 | 2.53 | 8.30 |
| Aldehyde | 44.52 | 17.53 | 50.27 | 44.37 |
| Alcohol | 9.43 | 39.16 | 22.27 | 7.08 |
| Formic acid ester | 3.79 | 6.70 | 5.99 | 12.08 |
| Ether + Ether aldehyde + Ether alcohol | 2.28 | 10.88 | 5.85 | 8.79 |

TABLE 4-continued (FIGS.: selectivity of monoolefin: %)

Example 4

|  | 1st reaction | 2nd reaction | Total | Comp. Example 7 |
|---|---|---|---|---|
| Acetal | 4.30 | 12.00 | 8.24 | 15.08 |
| High-boiling prod. 1) | 6.58 | 22.88 | 14.08 | 23.87 |
| Yield 2) |  |  | 72.54 | 51.45 |

1) High-boiling product: ether + ether aldehyde + ether alcohol + acetal
2) Yield = [aldehyde (mole) + alcohol (mole)]/monoolefin (mole) × 100 (%)

EXAMPLE 5

A. First Reaction Step and Separation of Unreacted Monoolefins and Paraffins

A flow chart of the reaction process by the use of an industrial continuous reactor is given in FIG. 1. As a starting material, butene dimers having the same composition as those of Example 2 were used. The butene dimers in which dicobalt octacarbonyl had been previously dissolved (1.5 g/kg as cobalt metal) were fed through pipe 1 in an amount of 1500 g/hour. Simultaneously, a compressed mixture of hydrogen gas and carbon monoxide gas ($H_2/CO=1.3$) was fed through pipe 2. The butene dimers and the mixture of hydrogen gas and carbon monoxide gas were sufficiently mixed in static mixer 4, and the resulting mixture was fed upward to oxo reaction column 5. The gas flow was controlled so that the upward linear velocity of the mixture in the reaction zone becomes 1 m/sec. or more.

The mixture discharged from reaction column 5 was cooled to 120° C. in heat exchanger 13, fed into cobalt-removing column 6 and brought into contact with a 1.2 wt % aqueous solution of sodium hydroxide fed from pipe 8. The amount of sodium hydroxide solution was controlled to give the sodium/cobalt equivalent ratio of 1.2–1.4. Most of the cobalt dissolved in the reaction mixture was removed in cobalt-removing column 6. After vapor-liquid separator 7 was depressurized, the reaction mixture was fed to washing column 9 and washed with water. Then, paraffins and unreacted butene dimers were separated from the mixture in 20-plate continuous distillation column 10 and accumulated in nitrogen-replaced receiver 11. The conversion of monoolefins in the first reaction step was 71.5%.

B. Second Reaction Step

After dicobalt octacarbonyl was dissolved in the mixture of unreacted butene dimers and paraffins accumulated in receiver 11 (4 g/kg as cobalt metal), the mixture was fed through pipe 1 in an amount of 1000 g/hour in the same manner as in the first reaction step. Simultaneously, a compressed mixture of hydrogen gas and carbon monoxide gas ($H_2/CO=1.3$) was fed through pipe 2. After the butene dimers and the gas mixture were mixed, water was fed through pipe 3 at a rate of 60 g/hour. The butene dimers, the mixture of hydrogen gas and carbon monoxide gas and water were sufficiently mixed in static mixer 4, and the resulting mixture was fed upward to reaction column 5. The gas flow was controlled so that the upward linear velocity of the mixture in the reaction zone becomes 1 m/sec. or more.

The mixture discharged from reaction column 5 was cooled to 120° C. in heat exchanger 13, fed into cobalt-removing column 6 and brought into contact with a 1.2 wt % aqueous solution of sodium hydroxide fed from pipe 8. The amount of sodium hydroxide solution was controlled to give the sodium/cobalt equivalent ratio of 1.2–1.4. Most of the cobalt dissolved in the reaction mixture was removed in cobalt-removing column 6. After vapor-liquid separator 7 was depressurized, the reaction mixture was washed with water. The conversion of monoolefins in the second reaction step was 91.3%. The compositions of the reaction products obtained in the first and second reaction steps of Example 5 are shown in Table 5. The composition of each reaction product was analyzed by gas chromatography under the same conditions as described above.

TABLE 5

(FIGS.: selectivity of monoolefin: %)

Example 5

|  | 1st reaction | 2nd reaction | Total |
|---|---|---|---|
| C8 paraffin | 2.58 | 5.73 | 4.21 |
| Olefin | 28.48 | 8.72 | 2.48 |
| Aldehyde | 51.56 | 25.94 | 58.95 |
| Alcohol | 7.80 | 32.20 | 16.97 |
| Formic acid ester | 3.27 | 11.89 | 6.66 |
| Ether + Ether aldehyde + Ether alcohol | 1.31 | 7.54 | 3.46 |
| Acetal | 5.00 | 7.98 | 7.27 |
| High-boiling prod. 1) | 6.31 | 15.52 | 10.73 |
| Yield 2) |  |  | 75.92 |

1) High-boiling product: ether + ether aldehyde + ether alcohol + acetal
2) Yield = [aldehyde (mole) + alcohol (mole)]/monoolefin (mole) × 100 (%)

What is claimed is:

1. A process for producing an alcohol or an aldehyde in which a monoolefin is used as a starting material to produce a saturated aliphatic alcohol or saturated alphatic aldehyde having one more carbon atom than the monoolefin, comprising:

a first reaction step of reacting the monoolefin with carbon monoxide and hydrogen in the presence of a cobalt carbonyl catalyst until the conversion of monoolefin reaches 50–90%;

a step of separating unreacted monoolefin from the reaction product obtained in the first reaction step; and a second reaction step of reacting the separated unreacted monoolefin with carbon monoxide and hydrogen in the presence of a cobalt carbonyl catalyst, wherein water is added only in the second reaction step.

2. The process according to claim 1 wherein the monoolefin is a straight-chain, branched or alicyclic monoolefin having 3–20 carbon atoms.

3. The process according to claim 1 wherein the reaction temperatures in the first reaction step and the second reaction step are independently from 120–200° C.

4. The process according to claim 1 wherein the reaction pressures in the first reaction step and the second reaction step are independently from 50–350 kg/cm².

5. The process according to claim 1 wherein the conversion of monoolefin in the second reaction step is 90% or more.

6. The process according to claim 1 wherein the cobalt carbonyl catalyst is removed from the reaction mixture by decomposition or extraction after the completion of the first reaction step.

7. The process according to claim 1 wherein water is used in the second reaction step in an amount of 0.5–30 wt % based on unreacted monoolefin.

8. The process according to claim 1 wherein the cobalt carbonyl catalyst is hydrocobalt tetracarbonyl or dicobalt octacarbonyl.

9. The process according to claim 1 wherein the molar ratios of hydrogen gas to carbon monoxide gas in the first reaction step and the second reaction step are independently from 0.8–2.0.

10. The process according to claim 1 wherein the cobalt carbonyl catalyst is removed from the reaction mixture by decomposition or extraction after the completion of the second reaction step.

11. The process according to claim 6 wherein the cobalt carbonyl catalyst is removed at a carbon monoxide partial pressure of 50 kg/cm$^2$ or more by using a 0.1–4 wt % aqueous solution of an alkali metal compound or alkaline earth metal compound in an amount giving the alkali metal/cobalt atomic ratio of 1–5 or the alkaline earth metal/cobalt atomic ratio of 0.5–2.5.

12. The process according to claim 10, wherein the cobalt carbonyl catalyst is removed at a carbon monoxide partial pressure of 50 kg/cm$^2$ or more by using a 0.1–4 wt % aqueous solution of an alkali metal compound or alkaline earth metal compound in an amount giving the alkali metal/cobalt atomic ratio of 1–5 or the alkaline earth metal/cobalt atomic ratio of 0.5–2.5.

* * * * *